US007322566B2

(12) United States Patent
Anthony

(10) Patent No.: US 7,322,566 B2
(45) Date of Patent: Jan. 29, 2008

(54) DEVICE FOR HEATING AND MOISTENING BREATHING AIR

(75) Inventor: Jean-Michel Anthony, Londerzel (BE)

(73) Assignee: BVBA Medisize Belgie, Antwerpen (BE)

( * ) Notice: Subject to any disclaimer, the term of this patent is extended or adjusted under 35 U.S.C. 154(b) by 162 days.

(21) Appl. No.: 10/515,860

(22) PCT Filed: May 27, 2003

(86) PCT No.: PCT/EP03/05556

§ 371 (c)(1),
(2), (4) Date: Jul. 5, 2005

(87) PCT Pub. No.: WO03/099366

PCT Pub. Date: Dec. 4, 2003

(65) Prior Publication Data

US 2005/0248045 A1    Nov. 10, 2005

(30) Foreign Application Priority Data

May 29, 2002  (EP)  .................................. 02447098

(51) Int. Cl.
*B01F 3/04* (2006.01)
(52) U.S. Cl. ...................... 261/128; 261/147; 261/154; 261/104; 128/201.13; 128/203.26
(58) Field of Classification Search ................ 261/128, 261/138, 139, 142, 147, 154, 94, 104; 128/201.13, 128/203.12, 203.17, 203.26, 203.27
See application file for complete search history.

(56) References Cited

U.S. PATENT DOCUMENTS 3,982,095 A * 9/1976 Robinson .................... 392/403

| 4,657,713 | A | * | 4/1987 | Miller | 261/142 |
| 4,753,758 | A | * | 6/1988 | Miller | 261/139 |
| 4,943,704 | A | * | 7/1990 | Rabenau et al. | 392/386 |
| 5,109,471 | A | * | 4/1992 | Lang | 392/396 |
| 5,383,447 | A |   | 1/1995 | Lang |  |
| 5,435,298 | A |   | 7/1995 | Anthony |  |
| 5,590,644 | A | * | 1/1997 | Rosenkoetter | 128/201.13 |

(Continued)

FOREIGN PATENT DOCUMENTS

EP    0413127 A    2/1991

(Continued)

*Primary Examiner*—Scott Bushey
(74) *Attorney, Agent, or Firm*—Knobbe, Martens, Olson & Bear, LLP

(57) ABSTRACT

A device for conditioning breathing air includes a housing (1) provided with an inlet (5) for non treated breathing air and an outlet (6) for the treated breathing air. The housing (1) contains a passive humidifier (7) and an active humidifier wherein the active humidifier includes a water supply inlet (13), a heating device for the supplied water, a membrane (12) having substantial water impermeable and water vapor permeable characteristics, and a heat exchange element (14). The membrane (12) is divided into a hydrophilic membrane (12a) and a water vapor permeable and water impermeable membrane (12b). The heat exchange element is a perforated metal plate (14) and/or a heating resistance. A method for the conditioning of breathing air includes the steps of: supplying through the inlet opening non treated breathing air, passively humidifying the supplied air through the passive humidifier, and actively humidifying the breathing air, through the active humidifier of a device.

21 Claims, 1 Drawing Sheet

U.S. PATENT DOCUMENTS

| | | |
|---|---|---|
| 5,906,201 A | 5/1999 | Nilson |
| 5,916,493 A * | 6/1999 | Miller .................... 261/154 |
| 5,970,210 A * | 10/1999 | Anthony .................. 392/386 |
| 6,010,118 A * | 1/2000 | Milewicz ................. 261/142 |
| 6,877,510 B2 * | 4/2005 | Nitta ..................... 128/203.17 |
| 6,918,389 B2 * | 7/2005 | Seakins et al. .......... 128/203.27 |

FOREIGN PATENT DOCUMENTS

| | | |
|---|---|---|
| WO | WO9707845 A | 3/1997 |

\* cited by examiner

DEVICE FOR HEATING AND MOISTENING BREATHING AIR

This application is the national stage of PCT/EP03/05556, filed under 35 USC 371 on May 27, 2003, which claims priority under 35 USC 119 to EP 02447098.1, filed May 29, 2002.

FIELD OF THE INVENTION

The present invention relates to devices for the conditioning of breathing air and more in particular to artificial noses.

BACKGROUND

Under physiological conditions, the nose functions to provide active warming and humidifying of breathing air. However, when a patient is undergoing artificial respiration the nose is shunted by a flexible tube, whose distal end is inserted into the trachea. In order to prevent unwanted effects such as cough stimulus or draining of the mucous membranes, the breathing air supplied must be treated. This is necessary, because the nose and throat mucous membranes, which normally take over this task, are no longer available under these circumstances. The moistening and warming treatment of the supplied breathing gases, which is essential for normal function of the lungs and nose, is nowadays performed by devices usually composed of an optional filtering apparatus and of a humidifying and heating apparatus, herein also referred as artificial noses.

Artificial noses are known in the art such as in EP 0 413 127, which described an apparatus for warming and moistening breathing air for artificial respiration wherein heating and humidifying are obtained by a combination of independent passive heat and moisture exchangers with an active heat and moisture exchanger. However, this device is relatively complex in design. WO 97/07845 discloses an apparatus for compensating heat and humidity loss in a device that administers or restitutes warm and humid air to a patient.

It is a main object of the present invention to provide a device for the conditioning of breathing air, which can maintain the heat level and the humidity proportion of said breathing air at the requested level. It is another object of the present invention to provide a device for the conditioning of breathing air wherein said air can be further filtered. It is a further object to provide a device for the conditioning of breathing air which is an all-in-one device having passive humidifying and active humidifying functions, which can be connected to an air supply duct at an arbitrary localization so that a very great flexibility of the device is assured. It is yet another object to provide a device for the conditioning of breathing air capable of preventing water condensation in said air supply duct so that the provision of water traps provided in all existing apparatuses until now are no longer needed.

SUMMARY OF THE INVENTION

The present invention relates to a device for conditioning breathing air comprising a housing provided with an inlet for non treated breathing air and an outlet for the treated breathing air, wherein in said housing passive humidifying means for passively humidifying said breathing air and active humidifying means for actively humidifying said breathing air are provided. In an embodiment of the present invention said passive humidifying means are arranged between said inlet and said outlet.

The active humidifying means in said housing may comprise a water supply inlet, a heating device for the supplied water and means for heat and moisture production. The present device is further characterized in that said means for heat and moisture production comprises a membrane having substantial water impermeable and water vapor permeable characteristics, and a heat exchange element able to provide a desired amount of heat to evaporate the thin layer of water.

In an embodiment of the present invention, the device for conditioning breathing air comprises a housing provided with an inlet for non treated breathing air and an outlet for the treated breathing air, wherein said housing comprises passive humidifying means and active humidifying means wherein said active humidifying means comprises a water supply inlet, a heating device for the supplied water, a membrane having substantial water impermeable and water vapor permeable characteristics, and a heat exchange element, characterized by the fact that said membrane is divided into a hydrophilic membrane and a water vapor permeable and water impermeable membrane, and that said heat exchange element is selected from the group comprising perforated metal plate and/or a heating resistance.

In an embodiment the heating device is arranged in a detachable manner on the housing of the device according to the invention. The water supply inlet is preferably connected to the housing such that a thin layer of water can be inserted between the heating device and the means for heat and moisture production. Said active humidifying means helps in compensating heat and humidity loss in said device. The water evaporation in thin layer permits water feeding by capillarity or gravity for example and further ensures precise vapor output by regulation of the temperature of the heating device.

In an embodiment of the present invention, said means for heat and moisture production is preferably provided perpendicularly to the flow of air thereby partially obstructing the air flow. The present device ensures a rapid and optimum conditioning of the air flowing through the device owing to the perpendicular positioning of the membrane and the heat exchange element with respect to the air flow. The air loads itself with water vapor produced by the action of the heating device on the water supplied between the heating device and the means for heat and moisture production.

The device of the present invention ensures that the correct humidity of the circulating air is always maintained, whilst warming and optionally filtering said air too. Furthermore, the device of the present invention provides the advantage of being space-saving and easy to handle. Indeed most prior-art devices are composed of a humidifying apparatus and a warming apparatus in the form of a water reservoir and of a heating means to vaporise the water, and optionally provided with evaporation means. The assembly of such parts is cumbersome, and provides with disadvantages when such apparatuses need to be replaced or cleaned. Moreover, mistakes may be made when connecting said assembly to an air supply and to a patient, as too many inlet, outlet and tubing are involved. The present invention provides with a passive humidifying unit and an active humidifying unit all combined in one device. Said device has the advantage of having at least one air inlet to be connected to the air supply and one air outlet to connect to a patient. As there is only one way to connect the new device, there can be no confusion. Moreover the device according to the invention has the advantage of having a heating device arranged in a detachable manner on the housing, providing thereby with a better control of the heating process and the possibility to easily remove and replace said heating device when needed.

The present invention will be further disclosed in detail hereunder wherein a preferred embodiment of the device of the present invention is disclosed in details. The description is only given by way of example and does not limit the invention. The reference numbers relate to the hereto-annexed figures.

DETAILED DESCRIPTION

The present invention relates to a device suitable for the conditioning of breathing air.

As used herein the term "breathing air" relates to any breathable gas suitable for an individual in need thereof, such as for example normal air to be supplied to the lungs of said individual. As used herein the term "individual" relates to animals, preferably 10 mammals, and more preferably human.

As used herein the term "conditioning of breathing air" and/or "treatment of breathing air" refers to the humidification/moisturizing and the warming of said air.

Figure 1:
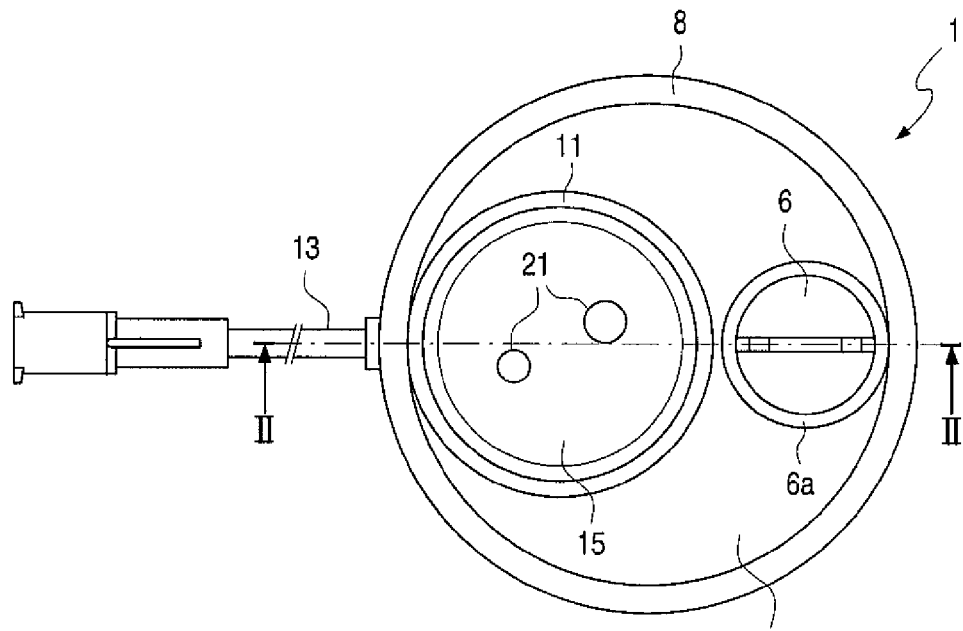
FIG. 1 represents a top-view of a preferred embodiment of a device according to the invention.
Figure 2:
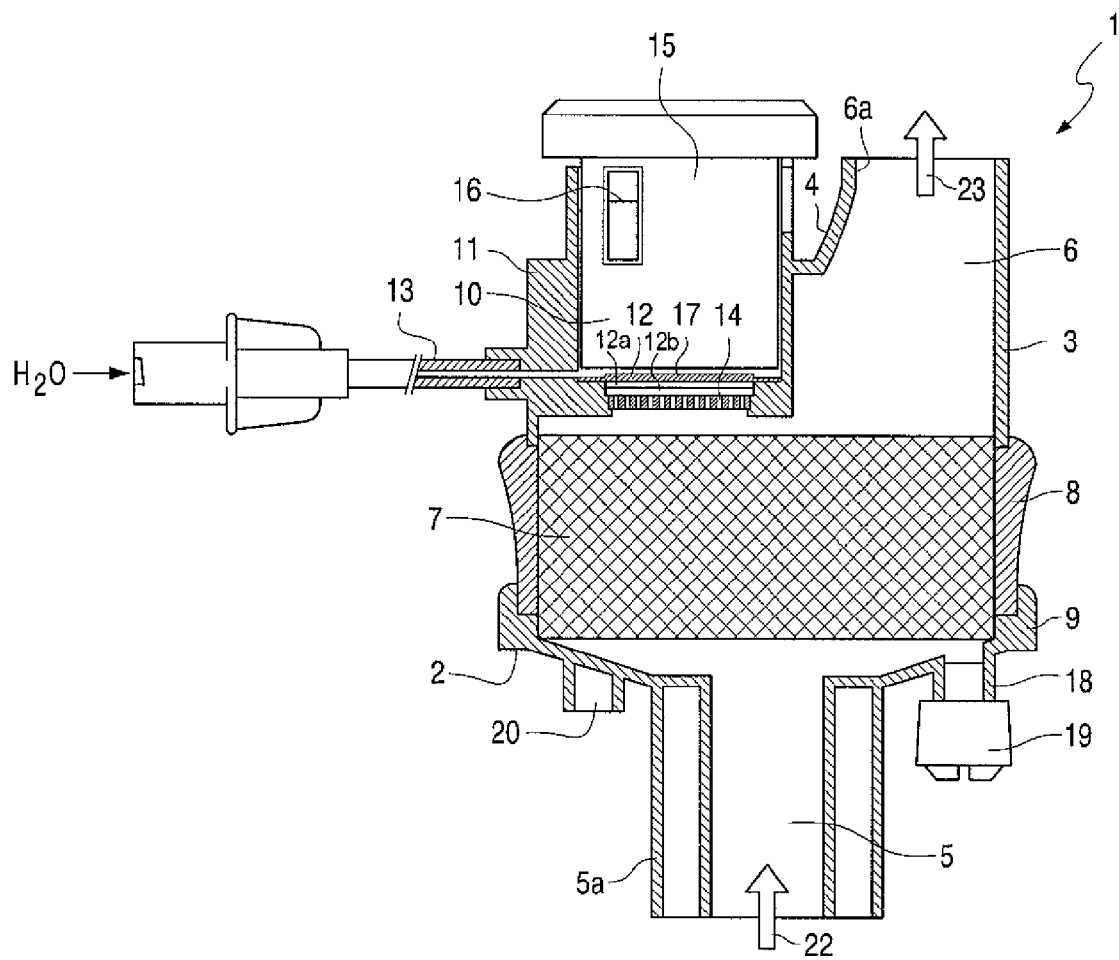
FIG. 2 represents a cross-sectional view along the line II-II of the device of FIG. 1.

An embodiment of said device is represented on FIGS. 1 and 2. Said device is composed of a housing 1 that is cylindrical in a preferred embodiment. The housing can be made of material suitable for medical uses. It is preferably made of plastic.

As shown FIG. 2, said device comprises a housing 1 having a bottom 2, a peripheral wall 3 and a cover 4, wherein said bottom 2 is provided with an inlet opening 5 for the supply of breathing air, said supply being illustrated by arrow 22. The cover 4 is provided with an outlet opening 6 wherefrom the treated breathing air exits as illustrated by arrow 23. Said device further comprises passive humidifying means 7 arranged in said housing 1 between said inlet 5 and said outlet 6, and a second opening 10 for the mounting of a heating device, a water supply inlet 13, and means for heat and moisture production. Suitable passive humidifying means can be made of any material known in the art such as polytetrafluoroethylene (PTFE). In an embodiment of the present invention said passive humidifying means 7 may be any heat and moisture exchanger (HME) known in the art. They may be made of a corrugated paper, or a spongy material or of a bundle of hollow fibres or multiple layer of PTFE which may be further treated with a hygroscopic material. In a preferred embodiment said passive humidifying means 7 comprises a heat and moisture exchanger made of corrugated paper. The device according to the invention may further comprise in said housing 1 a bacterial filter. Said bacterial filter may be made of hydrophobic or electrostatic material known in the art. Although the housing 1 in FIG. 2 is illustrated as being constructed from several separate components glued or fastened together, the present invention encompasses also a housing 1 formed from a single cast.

In an embodiment of the present invention, the means for heat and moisture production comprises a membrane 12 having substantial water impermeable and water vapor permeable characteristics, and a heat exchange element that assures a desired amount of heat.

On the bottom 2 and cover 4 of the housing 1, the openings 5 and 6 have connection pipes 5a and 6a respectively planned for attaching a tube. Said openings 5 and 6 and corresponding connection pipes 5a and 6a may be of identical or different sizes. The flow rate through said device may be modulated by adjusting the position and the size of the openings 5 and 6 and/or of the corresponding connection pipes. If a reduced flow out of the device is needed the size of the opening 6 can be reduced. The position of the openings 5 and 6 may also be adjusted so as to obtain the best conditioning of the air circulating through the device. Accordingly the position and size of the opening 10 can be adjusted so as to optimize the conditioning of the air flow.

The connecting pipe 5a can be connected to an air supply tube. By air supply tube must be understood the part of the tube that is connected to a non-illustrated anesthesia or a non illustrated respiratory apparatus. In a preferred embodiment as illustrated in FIG. 2, said connecting pipe 5a can be composed of two cylinders of different diameters which permit the adaptation of tubing of different diameters according to the application. The connecting pipe 6a can be connected to tubes, which supply air to a patient. The connecting pipes may be additionally heated so as to help the warming of the supplied breathing air.

Moreover, in another embodiment, as shown FIG. 2, the bottom 2 of the device according to the invention can have a further inlet 18. Said inlet 18 can be closed, in which case It is mounted by a stopper 19. Upon utilization of said inlet 18, the stopper 19, can be stored on a holding device 20 located on the bottom 2 of the device according to the invention.

This inlet 18 is suitable for sampling the air that circulates in the device according to the invention. Through said inlet 18, the device according to the invention may be connected to an air monitoring and/or analysis apparatus. When this option is not used, a stopper 19 can close the inlet 18. When the inlet 18 is in use, the stopper may be stored and kept on the holding device 20.

In another embodiment according to the invention said housing 1 may have a grip ring 8 surrounding the peripheral wall 3. Said grip ring 8 is mounted on said wall and secured with a flange 9 present on said wall 3. Both the grip ring 8 and the flange 9 are of such a shape as to form a groove. The presence of said grip and flange ring allows for the device to be seized particularly easily and surely. In case of replacement or cleaning of said device, this provides for the easy handling of the device according to the invention. Said device can be securely seized from the side, so that slipping is practically impossible. The connecting and disconnecting of said device becomes easy to perform and problem free.

The device according to the invention is further characterized in that the housing 1 is provided with second opening 10 provided with walls 11. The opening 10 is suitable for the mounting of a heating device. The walls 11 are preferably designed such as to be double walls arranged in a concentric way. Such design will help in the cooling of the housing when the heating resistance is on, and act as thermal insulation means. Said opening 10 is provided with means for heat and moisture production. In a preferred embodiment said means for heat and moisture production comprises a membrane 12 having substantial water impermeable and water vapor permeable characteristics, and a heat exchange element that assures a desired amount of heat. In a preferred embodiment said element is a perforated metallic plate 14.

Furthermore a water inlet 13 is connected to the housing between the heating device and the membrane 12. The water can flow through by simple capillarity, diffusion, active pumping and/or by gravity. The water inlet 13 can be further provided with a flow restrictor. Said flow restrictor may be a capillary tube of such a dimension as to allow the flow of 3 to 15 ml/h more preferably of 6 to 8 ml of water per hour.

According to an embodiment of the present invention the membrane 12 is divided into a hydrophilic membrane 12a and a water vapor permeable and water impermeable membrane 12b. Said membrane 12b is of a material that is water impermeable and water vapor permeable, and is preferably placed between the hydrophilic membrane 12a and the metal plate 14. The use of the membrane 12b allows, only water vapor to enter the device and the entrainment of water droplets by the air stream passing through said device is avoided. Said membrane 12b can be made of any material known in the art with water impermeable and water vapor permeable characteristics such as PTFE. For example said membrane 12b can be made of Gore-Tex which is a dispersion-polymerized PTFE. The hydrophobic nature of the PTFE allows for the liquid water to be repelled from the pores, whereas water vapor can pass through.

As shown FIG. 2, said heating device comprises a component 15, whereof a flat side 17, is directed towards said membranes 12. In an embodiment, said flat side 17 conveys the heat and the casing of component 15 is thermally insulated. Said heating device can be a self-adjusting resistance of the PTC-type. Although not shown in FIG. 2, said component 15 is connected in any convenient manner to an electrical source of energy through power cables. Said component 15, has furthermore at least two holes 21 for the plugging of said power cables and for the plugging of LED (Light Emitting Diode) indicator. On the flat side 17 of the component 15 at least one transversal canal can be provided. Said component 15 can be further provided with a microswitch 16 which can be activated by a sliding movement or pressure, thereby switching on the heating device.

Said heating device can be integrated in the housing of the device according to the invention thereby forming one piece, which may be disposable as a whole. In another embodiment said heating device can be detachably mounted in said housing, providing for an easy removal or replacement, and further allowing the reutilization of the heating device upon disposal of the device according to the invention.

The housing 1 comprises active humidifying means for compensating heat and humidity loss obtained by fitting the component 15 of the heating device in the opening 10. The hydrophilic membrane 12a in said housing thereby rests on the flat side 17 of the component 15.

The mounting of the component 15 of the heating device in the opening 10, can be realized by using known means, such as a sealing O-ring (not shown), and/or a bayonet catch. The O-ring can be mounted in a circular excavation of the wall of the component 15. In a preferred embodiment the fitting is realized using a sealing O-ring and a bayonet catch.

To achieve the maintenance at the desired level of heat and humidity of the air that must be administered to a patient, a membrane 12a with hydrophilic characteristics rests on the flat side 17 of the heating device. Hereupon rest then a second membrane, namely a water impermeable and water vapor permeable membrane 12b. Both membranes can appear as a composite material, so that both membranes form a whole membrane 12.

The water that must be admitted for the humidification of breathing air reaches the interior of the opening 10 via a water supply duct 13 connected to the housing 1.

As can be derived from FIG. 2, the water can flow in the opening just under the already earlier mentioned membranes 12a and 12b but above the flat side 17 of the heating device, thereby forming a thin layer of water. The flat side 17 of the heating device may have at least a transversal canal, which can help to ensure an ideal diffusion of the water in the hydrophilic membrane 12a. The water supplied through the water supply duct 13, can then be diffused homogeneously and uniformly over the flat side 17 of the heating device and soaks the hydrophilic membrane 12a that rests on this flat side 17.

Since the membrane 12b shows water impermeable and water vapor permeable characteristics, the desired level of water vapor will be able to displace itself through this membrane. Membranes with such characteristics are known. They can be made of porous P.T.F.E. glued to a support of micro glass or polyester fibers. Other membranes with the same characteristics can be used herein.

In order to maintain the largest possible quantity of humid air brought at the desired temperature at a constant level and to supply it in this state to a patient, said membrane 12b rest on a perforated metal plate 14. Condensation can then be reduced or prevented by the help of the perforated metal plate 14. Said plate 14 works as a heat exchanger, ensuring the circulation air is maintained at the correct temperature not only by the water vapor produced but also by this plate. The same object could be achieved by replacing said metal plate 14 by an additional self-adjusting electric heating resistance. Said perforated metal plate 14, moreover has a further protecting role and help preventing the damaging or perforating of the membranes 12.

The heat exchange processed by the metal plate 14 can be bi-directional and can thus influence by its feedback characteristics the self-adjusting function of the heating device, so that in case of a greater airflow this device will evaporate a greater quantity of water. The heating device can be resistances of the P.T.C. type, it may be detachably mounted in the housing of the device, or in another embodiment may be integrated as a whole into the housing of said device.

The present invention provides therefore a device allowing the conditioning of breathing air namely the passive and active humidification and the heating of said air, and further allowing an optional filtration of said air. Said device is preferably made of one piece of material, it is easy to handle, connect and disconnect. It is also suited for a single use and can be disposable. Moreover by strictly maintaining the temperature of the humid air in the device under control, the formation of too much condensation water herein can be prevented.

Said device clearly help in maintaining at the desired heat level the water vapor in the tubes that administer or restitute air to a patient and assuring a humidity level whereby a minimum of condensation occurs in these tubes.

Said device can therefore be used as an artificial nose, in all applications requiring the humidification and heating and optionally the filtration of air. Said device according to the invention is thereby suitable for the treatment of breathing air. It can be connected to a breathing apparatus that administer or restitute air to a patient. Said device can further be used in combination with an air monitoring or analyzing device.

The present invention further relates to a method for the conditioning of breathing air, comprising the step of connecting a device according to the invention, to an air supply and running the air through said device. The present invention also relates to a method for the conditioning of breathing air, comprising the steps of supplying through the inlet opening non treated breathing air, passively humidifying said supplied air through the passive humidifying means, and actively humidifying said breathing air, through the active humidifying means of a device according to the invention.

The invention claimed is:

1. A device for conditioning breathing air, the device comprising a housing provided with an inlet for non treated breathing air and an outlet for the treated breathing air, an air flow path being defined between said inlet and said outlet, wherein said device comprises a passive humidifier and an active humidifier wherein said active humidifier comprises a water supply inlet, a heating device for the supplied water, a membrane having substantial water impermeable and water vapor permeable characteristics, and a heat exchange element having a perforated metal plate, and wherein said membrane is divided into a hydrophilic membrane and a water vapor permeable and water impermeable membrane, and wherein said heat exchange element and said membrane are perpendicularly positioned and offset with respect to said air flow path so as to not significantly occlude said air flow path.

2. A device according to claim 1, wherein said passive humidifier is arranged between said inlet and said outlet.

3. A device according to claim 1, wherein said passive humidifier is a heat and moisture exchanger.

4. A device according to claim 1, wherein said device additionally comprises a bacterial filter.

5. A device according to claim 1, wherein said heating device is arranged in a detachable manner on the housing.

6. A device according to claim 1, wherein said water supply inlet is connected to the housing such that a thin layer of water is able to be inserted between the heating device and said membrane having substantial water impermeable and water vapor permeable characteristics.

7. A device according to claim 1, wherein the housing comprises a bottom connected to a peripheral wall and a cover connected to the peripheral wall, wherein said bottom is provided with an inlet opening for the supply of breathing air, and wherein said cover is provided with an outlet opening for the treated breathing air, and with a second opening for the mounting of a heating device.

8. A device according to claim 1, wherein said heat exchange element further comprises a perforated metallic plate.

9. A device according to claim 1, wherein the membrane is of a material that is water impermeable and water vapor permeable, placed between the hydrophilic membrane and the metal plate.

10. A device according to claim 1, wherein said heating device comprises a component, whereof a flat side, is directed towards said membranes.

11. A device according to claim 10, wherein one of said membranes is a hydrophilic membrane that rests on the flat side of the component.

12. A device according to claim 10, wherein the component is mounted in the opening.

13. A device according to any claim 10, wherein the component has a sealing O-ring and/or a bayonet catch for the fitting in the opening.

14. A device according to claim 10, wherein the component has a microswitch.

15. A device according to claim 7, wherein said inlet and outlet openings have a connection pipe for attaching a tube.

16. A device according to claim 7, wherein said bottom has a further inlet.

17. A device according to claim 16, wherein said inlet is mounted by a stopper.

18. A device according to claim 17, wherein said bottom has a further holding device for said stopper.

19. A device according to claim 7, wherein said housing has a grip ring and a flange surrounding said peripheral wall.

20. A method for the conditioning of breathing air flowing through a device having an air flow path passing air substantially directly through the device between an air inlet and an air outlet along said air flow path, comprising passively humidifying said breathing air; actively humidifying said breathing air, wherein said active humidifying comprises:

passing heated water vapor through a hydrophilic membrane portion and a liquid water impermeable membrane portion. said hydrophilic membrane portion and said liquid water impermeable membrane portion being perpendicularly positioned and offset with respect to said air flow path so as to not significantly occlude said air flow path; and passing said heated water vapor through a heat exchange element and into said breathing air, said heat exchange element being perpendicularly positioned and offset with respect to said air flow path so as to not significantly occlude said air flow path.

21. A device for conditioning breathing air, the device comprising a housing provided with an inlet for non treated breathing air and an outlet for the treated breathing air, an air flow path being defined between said inlet and said outlet, wherein said device comprises a passive humidifier and an active humidifier wherein said active humidifier comprises a water supply inlet, a heating device for the supplied water, a membrane having substantial water impermeable and water vapor permeable characteristics, and a heat exchange element having a heating resistance, and wherein said membrane is divided into a hydrophilic membrane and a water vapor permeable and water impermeable membrane, and wherein said heat exchange element and said membrane are perpendiculary positioned and offset with respect to said air flow path so as to not significantly occlude said air flow path.

* * * * *